United States Patent [19]
Horstmann

[11] 4,323,810
[45] Apr. 6, 1982

[54] IRRADIATION APPARATUS INCLUDING A LOW-PRESSURE MERCURY LAMP WITH FLUID MEDIUM DUCT MEANS

[76] Inventor: Georg Horstmann, Gerbelstr. 19, 4902 Bad Salzuflen, Fed. Rep. of Germany

[21] Appl. No.: 44,772

[22] Filed: Jun. 1, 1979

[30] Foreign Application Priority Data

Jun. 5, 1978 [DE] Fed. Rep. of Germany ....... 2825018

[51] Int. Cl.³ .......................... H01J 61/33; H01J 61/52
[52] U.S. Cl. ......................................... 313/24; 313/36; 313/44; 313/220; 250/436
[58] Field of Search ................... 313/493, 220, 44, 24, 313/35, 36, 22; 250/436, 532, 541

[56] References Cited

U.S. PATENT DOCUMENTS

| | | | |
|---|---|---|---|
| 1,969,655 | 8/1934 | Mailey | 250/436 X |
| 2,317,265 | 4/1943 | Foerste et al. | 313/220 X |
| 2,364,889 | 12/1944 | Blair | 313/220 X |
| 2,482,421 | 9/1949 | Lemmers | 313/493 X |
| 3,451,579 | 6/1969 | Bishop | 313/220 X |
| 4,101,777 | 7/1978 | Reid | 250/436 |
| 4,195,249 | 3/1980 | Ariga et al. | 313/493 |

FOREIGN PATENT DOCUMENTS

| | | | |
|---|---|---|---|
| 502726 | 7/1930 | Fed. Rep. of Germany | 250/436 |
| 1000521 | 1/1957 | Fed. Rep. of Germany | 313/220 |

*Primary Examiner*—Palmer C. Demeo
*Attorney, Agent, or Firm*—Manfred M. Warren; Robert B. Chickering; Glen R. Grunewald

[57] ABSTRACT

An irradiation apparatus is disclosed in which a low-pressure mercury lamp having a flat, elongated lamp tube is provided that is suitable for high intensity photochemical disinfecting and sterilization of materials. The irradiation apparatus includes a flat outer envelope, surrounding the lamp tube and ducts positioned along the narrow sides of the lamp tube to permit cooling of the apparatus and optionally the efficient generation of ozone. Various structures into which the apparatus may be incorporated for the immersion irradiation of fluids are also disclosed.

9 Claims, 14 Drawing Figures

IRRADIATION APPARATUS INCLUDING A LOW-PRESSURE MERCURY LAMP WITH FLUID MEDIUM DUCT MEANS

Low-pressure vapour lamps usually consist of a quartz tube with two electrodes at the ends and are filled with a metal vapour at a vapour pressure of e.g. 0.1 torr. The quartz tube is encased in an enveloping tube and may also be cooled. In operation an arc discharge develops between the two electrodes and is used to generate light. Among low-pressure vapour lamps, low-pressure mercury lamps make up a very large proportion because they are very suitable instrments for generating UV radiation. That is to say, the light they emit is a pure line spectrum showing a high UV content and possessing a particularly strong line at 254 nm.

Recently the conducting of photochemical reactions with the aid of UV radiation has been acquiring ever greater importance; photochemical disinfecting and sterilization operations constitute a particularly important area in this respect. A number of these reactions, and especially photochemical disinfecting and sterilization processes, show a marked dependence on the radiation intensity, so that maximum radiation intensity becomes of paramount importance. This is because the reactions in question require the simultaneous presence of a certain minimum number (e.g 4 or 5) of light quanta at the molecular site of the reaction, and hence when a radiation of low intensity is applied, i.e. one that is unable to furnish this minimum number of light quanta simultaneously, these reactions cannot take place. Nor can this situation be remedied, e.g. by extending the irradiation time.

Especially for these highly intensity-dependent reactions, the existing low-pressure mercury lamps are not especially suitable, since practically speaking the radiation density emitted at their outer surfaces cannot be increased above a certain maximum of approximately 30 mW/cm$^2$. Often this was not sufficient, especially when, in the interest of a technically reasonable reaction conversion, generally the space to be irradiated must not be too small in volume. In these cases, therefore, the difficulty has been overcome by concentrating the radiation from several lamps, possibly with the aid of reflectors, onto the same reaction space. This is very expensive, however, and also results in a poor energy balance sheet.

Now, with the invention it is intended to create a low-pressure vapour lamp, especially a low-pressure mercury lamp, which can emit a substantially higher radiation density over a large radiation area and which permits the designing of better and more efficient irradiation units. The invention attains this goal in an astonishingly simple manner by designing the tube of the low-pressure mercury lamp with a flat, elongated cross-section and extending the electrodes in the direction of the lamp-tube width.

The invention is based on the logical exploitation of the fact that the relatively low radiation density emitted by traditional low-pressure mercury lamps is due to the hitherto always round cross-section of the lamp tube. As a consequence the radiating plasma in the lamp tube is compelled to adopt the shape of a cylinder, which possesses a small surface area in relation to its volume. The consequence of this is that the radiation generated in the inner core of the plasma is largely absorbed again in the outer layers of the plasma and is thus lost as heat, so that for all practical purposes only the radiation generated in the outermost layer of plasma can be usefully emitted to the outside. This phenomenon is largely independent of the diameter of the tube, and hence the diameter is kept very small; then, however, we have the disadvantage of a much too small total radiation output.

In the case of the invention, however, there is no inner absorption of part of the radiation generated, since the luminous plasma now has the shape of a "board", i.e. a body of great width and only small depth. Thus practically all the radiation generated can be emitted usefully to the outside, mainly over the two wide sides of the lamp tube, and the result is a lamp with a larger radiation area (compared with a round lamp of equal cross-sectional area) and with a substantially increased radiation density, which, for equal energy consumption, can be more than twice the values hitherto attainable. Surprising, at the same time, is the extraordinarily high stability of the luminous plasma.

It is also a special advantage of the invention that the heat generated by absorption of radiation is eliminated. For this reason, and because in any case a tube of flat, elongated cross-section is easier to cool than a corresponding round tube, the lamp can be driven at a much higher wattage than before, whereby the radiation density can be still further increased quite considerably.

The fact that the invented lamp emits its radiation for the most part only along its two wide sides, where it does so with extremely high radiation density, permits the designing of irradiation units which can be fitted with one or more of the invented lamps and which are designed so that the medium to be irradiated flows through a reaction housing of substantially rectangular flow cross-section. The lamp or lamps are then placed in the reaction housing in such a way that their broad sides cover the flow path of the medium. Such irradiation units are not only easy to manufacture in various embodiments, but, since they are optimally adapted to the radiation geometry of the lamps, they possess extremely high efficiency. Furthermore, they afford additional advantages.

Alternatively, an arrangement can be made with the invented lamp such that the lamp is installed in a closed enveloping tube and is used as an immersion lamp for the irradiation of flowing or stationary media. Here again numerous advantages are attainable.

A typical field of application of the invented lamp or of irradiation units fitted therewith is the UV sterilization of water, for which the strong wavelength of 254 nm is particularly important. Of course, many other fields of application are possible, including ones in which traditional lamps or round design are relatively or totally ineffective. For example, owing to its high radiation density and its favourable geometry, ozone can be produced with the invented lamp, provided the lamp tube is made of a material that is sufficiently transmissive for the wavelength range of about 180-200 nm.

It is known that ozone forms when gaseous oxygen is subjected to UV radiation. Hitherto, however, the yield has been small, so that in practice other methods (e.g. the action of electrical corona discharges on oxygen) have been preferred for the generation of ozone. The poor efficiency of ozone production by means of UV radiation is due, amongst other factors, to the fact that the initially formed ozone breaks down again during prolonged exposure especially to the wavelength 254 nm. Since for generating ozone by UV radiation it was hitherto necessary to conduct the oxygen or gas containing oxygen in the axial direction of a round lamp tube (surrounded by a corresponding enveloping tube), this decomposition process was unavoidable, even when a very short lamp tube was employed. The ozone yields, therefore, were always less than 0.15 g per 20 W lamp output. With the invented lamp, however substantially higher yields of gaseous ozone can be attained, and moreover, in the irradiation unit fitted therewith it is even possible to convert water-dissolved oxygen directly into ozone.

Details of the invention and its advantages are explained in greater detail hereinafter in connection with embodiments illustrated in the drawings, where:

In all figures similar parts are denoted by the same reference number and functionally similar modifications of these parts are characterized by supplementary indices.

Figure 1:
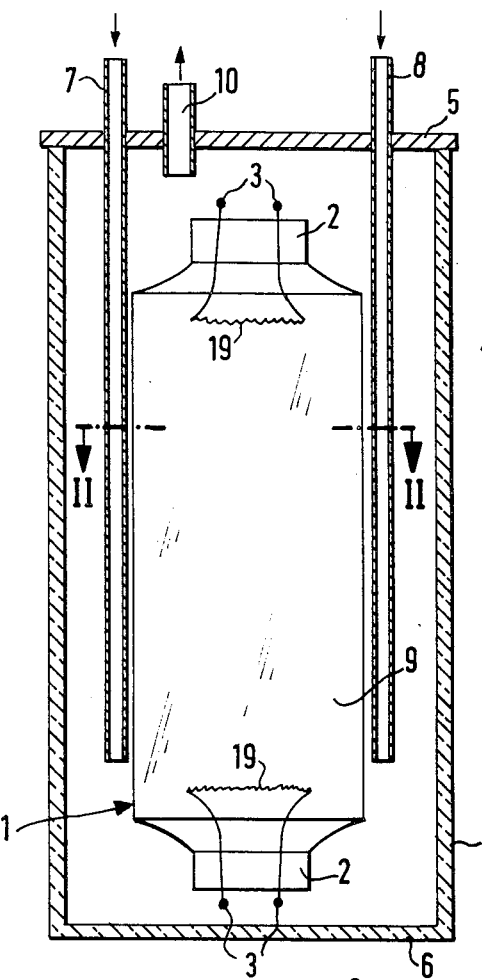
FIG. 1 is a schematic representation of a first embodiment of the invented lamp together with an irradiating set-up designed as an immersion tube.
Figure 2:
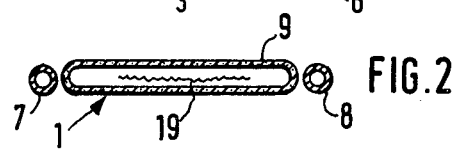
FIG. 2 is a section in the plane II—II of FIG. 1.

FIG. 1 shows a low-pressure mercury lamp 1, the tube 9 of which, as seen best in FIG. 2, possesses a flat, elongated cross-section and is made of quartz glass or other suitable UV-transmitting material. At both ends the tube is fitted with holders 2 through which, in both cases, two electrode connections 3 are passed, between which an elongated electrode 19 is stretched in the direction of the width of the tube. The external electrode connections are not shown. Lamp 1 is filled with mercury vapour in the usual low-pressure range.

Lamp 1, shown in FIG. 1, if designed for 220 V operating voltage, can have a cross-sectional area of approximately 10×30 mm and an effective length of about 80 cm. Electrodes 19, depending somewhat on the electrode material employed, are about 15–20 mm long. When such a lamp is operated at a wattage of e.g. 120 W, it yields a radiation density of more than 260 mW/cm$^2$, i.e. more than ten times that of a traditional lamp of round design. As an additional important advantage, the radiation is emitted for the most part only on the wide sides of the lamp tube, i.e. perpendicularly to the longitudinal central plane of the lamp.

Figure 6:
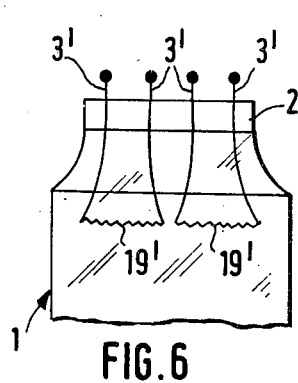
FIG. 6 is a schematic representation of a modified embodiment of the invented lamp.

The power consumption of lamp 1, of course, cannot be increased arbitrarily, because after a certain limiting value, which in the case of the above numerical example lies at about 150 W, the luminous plasma arc becomes unstable. It is possible, however, to keep the luminous plasma stable even at higher power consumption values, if, as represented in FIG. 6, in place of a single electrode 19 at each end of the lamp, two or more independent electrodes 19' are provided and the lamp tube is widened accordingly. With two pairs of electrodes, and hence two plasma arcs per lamp, the power consumption of the lamp can immediately be increased, relative to the previous example, to 250 W, which—since the lamp tube does not have to be doubled in width—results in a further increase of radiation density, as well. With three and more pairs of electrodes, correspondingly still higher outputs of lamp 1 are achievable without difficulty.

Since lamp 1, regardless of whether its electrodes are designed according to FIG. 1 or FIG. 6, emits its radiation similarly on both wide sides of the lamp tube, for UV irradiation of fluids, e.g. for the UV sterilization of water or the like, its use as an immersion lamp is preferred. In the example of FIG. 1 lamp 1 (which can also have the alternative design according to FIG. 6) is therefore encased in an enveloping tube 4 which must also be made of quartz or a corresponding material. This enveloping tube has a cross-sectional shape adapted to lamp 1, i.e. a flat, elongated shape, and is sealed on all sides, e.g. by a cover 5 or, as indicated at the lower end of FIG. 1, by an integral end wall 6. Through cover 5, in the example according to FIG. 1, are passed two cooling pipes 7 and 8 which extend along the two narrow sides of lamp 1 and e.g. are charged with a cooling gas. The cooling gas flows through pipes 7 and 8, leaves these at the lower end, and then flows back into the space between lamp 1 and enveloping tube 4 to exit through an outlet 10 in cover 5.

It is not absolutely necessary to cool lamp 1, and further below embodiments with uncooled lamps are described. If cooling is provided it does not necessarily have to take place in the manner described above. For example, cooling can also be carried out by joining pipes 7 and 8 together at their lower ends and permitting cooling water to flow through them, in which case one of the pipes acts as the input and the other as the outlet.

Figure 3:
FIG. 3 is a corresponding section for a somewhat modified embodiment of the lamp.

It is also possible to incorporate the cooling pipes in lamp 1, as shown in FIG. 3, by providing two compartments 7' and 8' along the two narrow sides of lamp tube 9' and causing a cooling medium to flow through them. What is important in either case is that the cooling pipes, whether they are separate pipes or incorporated in the lamp, should run along the narrow sides of the lamp so as not to interfere with the surface radiation of high density being emitted from the two wide sides. The radiation emitted from the two narrow sides, which in any event is only a very small proportion of the total radiation, can only be utilized much more awkwardly (e.g. with the aid of added reflectors), so that the cooling pipes in this area do not really interfere at all.

In a somewhat modified form the irradiation set-up represented in FIG. 1 (with lamp 1, the electrodes of which may be designed as in FIG. 1 or in FIG. 6) can also be used very effectively for the production of ozone in the gaseous phase. For this purpose it is merely necessary to make lamp tube 9 from a quartz which is also sufficiently transmissive to the wavelength 183 nm and to provide, in place of cooling pipes 7 and 8 according to FIG. 1, two product conducting pipes which are so designed that oxygen (or a gas containing oxygen) can flow transversely over the wide sides of lamp tube 9, i.e. from one narrow side to the other. In this way the irradiated gas can be removed after a very short sojourn from the radiation region, i.e. before the radiation of wavelength 254 nm, which breaks down the ozone again, can become effective to an appreciable extent, and in this way the ozone yield is considerably increased. At the same time, it is possible to employ the set-up as a pure ozone generator and to optimize the operating conditions with a view to this application. Equally possible, however, is a combined use where ozone is produced and the lamp radiation can also be exploited for other photochemical reactions. Especially for the case of sterilization of fluids, e.g. water, such a combined use is favourable where, for example, lamp 1, fitted with a UV-transmitting envelope tube is immersed in the water and at the same time is exposed to a flow of oxygen or oxygen-containing gas in the above-described "transverse flow" pattern, whereupon the ozone generated is passed into the water at another location for purposes of pre- or post-sterilization. An application of this kind is not possible with traditional low-pressure mercury lamps.

Figure 4:
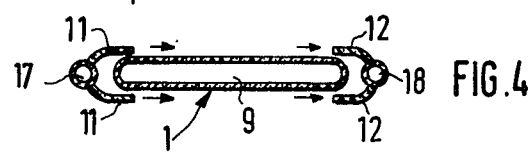
FIGS. 4 and 5 are each one section corresponding to FIG. 2 for radiation set-ups to produce ozone in the gaseous phase.

If lamp 1 is intended to produce gaseous ozone as a by-product in the course of UV sterilization in the manner described above, product-conducting pipes 17 and 18 are expediently arranged in the manner shown in FIG. 4 similarly to pipes 7 and 8 shown in FIG. 1, but are closed at their lower ends and are in addition furnished at intervals with nozzles 11 and 12 which open parallel to the two wide sides of the lamp tube. When oxygen or a gas containing oxygen, e.g. air, is fed under moderate pressure through e.g. pipe 17 with nozzles 11 and is drawn off in the form of a gas containing ozone by gentle suction through the other pipe 18 with its nozzles 12, this arrangement ensures that the irradiated gas, at least in the area of the coacting pairs of nozzles, will be conducted in a sufficiently good transverse flow across the lamp tube, i.e. that it will be removed quickly enough from the influence of the radiation. Correspondingly high ozone yields result.

Figure 5:
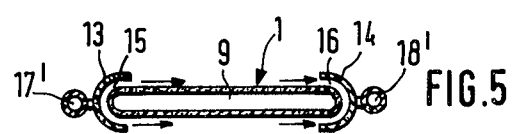

For generating gaseous ozone alone, a lamp of the design of FIG. 5 is preferred. In this lamp two half shells 13 and 14 are provided which envelope the two narrow sides of lamp tube 9, leaving two equally large gaps 15 and 16, and which are made of high-grade steel or a corresponding ozone-resistant material. One of the two annular gaps, e.g. gap 15 inside half shell 13, is charged under pressure with gas containing oxygen, while the other annular gap 16 serves to draw off the ozone-containing gas. Thus the two wide sides of lamp tube 9 are exposed to an excellent transverse flow which, depending on the width of the lamp tube is only a few centimeters in length and also possesses a maximum layer thickness of only about 3 mm. To feed and draw off the gases product conducting pipes 17' and 18' are joined at intervals along lamp tube 9 to the two annular gaps 15 and 16.

In order to prevent the gas flowing in annular gaps 15 and 16 in the axial direction of lamp tube 9 from being exposed to the wavelength 254 nm, which is especially harmful to ozone, the two narrow sides of lamp tube 9 can be rendered opaque by blackening or by the installation of a second half shell of metal on both sides, which then bounds the annular gap on the lamp tube side. Similarly, the two inner faces of the two half shells 13 and 14 can be provided with a reflection-reducing coat, in the event that the half shells are made of a UV-reflecting material. It is also expedient, in the case of the embodiment according to FIG. 4, to render the two narrow sides of the lamp tube opaque when pipes 17 and 18, with nozzles 11 and 12, are not made of metal, but e.g. of quartz glass. In addition, for use as an ozone generator only an enveloping tube 4 of UV-transmitting material need not be provided. An enveloping tube of high-grade steel will then suffice.

On the other hand, if it is not required to produce gaseous ozone, but only to irradiate fluids, or possibly gases, with UV rays, e.g. for the UV-sterilization of water or the like, it has been found advantageous to install a number of lamps 1 designed according to FIG. 1 or FIG. 6 without added cooling equipment as immersion lamps in an irradiation unit of rectangular cross-section with a fluid flowing through it. Rectangular flow cross-sections are optimally adapted to the radiation geometry of the lamps, because lamps 1 emit their radiation essentially only from their wide sides perpendicularly to the central longitudinal plane of the lamps. Also, such units are extraordinarily inexpensive to manufacture (e.g. from high-grade steel, or possibly even from Teflon) and permit a manner of construction whereby the individual lamps can be quickly and easily replaced even in the course of operation.

Figure 7:
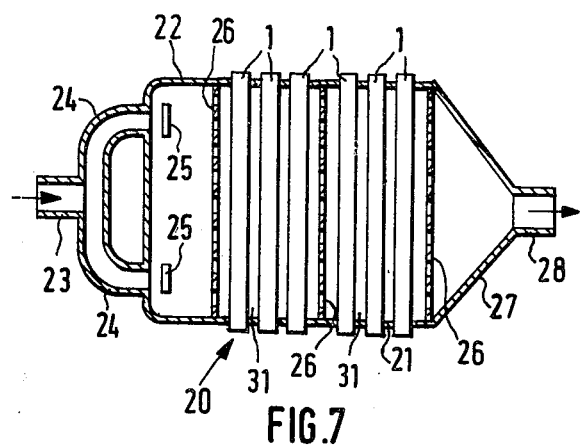
FIGS. 7 and 8 are schematic representations in plan view and side elevation, respectively, of an irradiation unit for flowing media.
Figure 8:
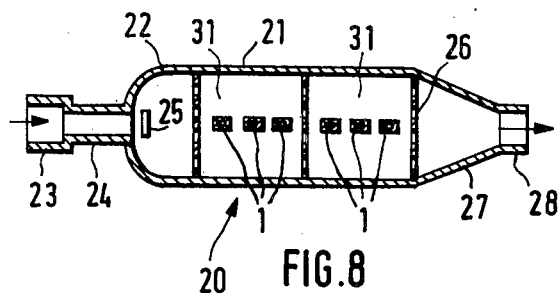

A typical example of such an irradiation unit 20, intended for the UV sterilization of water is illustrated in FIG. 7 is plan view, and in FIG. 8, in side elevation. A flat-lying, elongated unit housing 21 of rectangular cross-section is provided through which water flows in the longitudinal direction. In the central longitudinal plane 21, extending transversely to the direction of flow of the water, i.e. across the width of housing 21, are a number of lamps 1 designed according to FIG. 1 or FIG. 6. At the input end housing 21 has an inlet section 22 which has the function of distributing the flow arriving from round input pipe 23 as uniformly as possible and without the development of flow filaments that pass through the unit at different velocities. This inlet section 22 is essentially of box design, its cross-section corresponding to the cross-section of housing 21, and it is connected to input pipe 23 through two connecting pipes 24. In front of each of the exits of connecting pipes 24 there is a baffleplate 25. Inlet section 22 is connected to housing 21 through an orifice plate 26. At the exit end housing 21 connects with outlet pipes 28 through an exit cone 27.

The interior of unit 20 may comprise a single irradiation chamber, but in many cases it is expedient to subdivide the interior of the housing by means of additional orifice plates 26 so that a series of irradiation chambers in cascade arrangement is formed, each chamber containing two or three lamps 1. This affords the advantage that with increasing number of chambers in cascade arrangement the dwell period spectrum of the flowing water becomes progressively narrower, i.e. the actual dwell time of any given element of volume is made to approximate very closely its specified mean average dwell time in the unit. This ensures a particularly uniform treatment of all elements of volume of the flowing water. In general 3 to 5 compartments in cascade arrangement suffice. Of course a cascading effect can also be achieved by arranging a corresponding number of undivided housings 21, i.e. ones that constitute only a single irradiation chamber, one behind the other, but then the structural length of the whole unit becomes greater.

Figure 9:
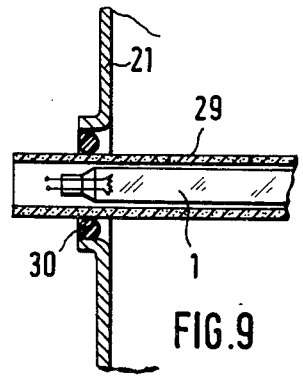
FIG. 9 is a detail of the unit according to FIGS. 7 and 8 in enlarged scale.

The separate lamps 1 can be installed directly with a suitable seal in suitable openings in the wall of housing 21. At times, however, this can result in an excessive cooling of lamps 1, and furthermore replacement of burned-out lamps, when necessary, is then possible only with an interruption in the operation of the unit. It is preferable, therefore, as in FIG. 9, to incorporate in housing 21 an enveloping duct 29 extending from one housing wall to the opposite one, and which is made of the same UV-transmitting material as the lamp tube, and which is sealed against the housing wall with a packing 30 in such a way that both its ends are freely accessible from the outside. Ducts 29 are slightly larger than lamps 1, so that the latter slide easily into them and can be removed again without the necessity of emptying the irradiation unit. It is true that the enveloping ducts result in a slight loss of radiation, but this is of little importance on account of the extremely high radiation output of lamps 1 and is more than compensated by the advantages of the enveloping ducts.

If both lamps 1 and enveloping ducts 29 in irradiating unit 20 are made of a quartz material that also transmits wavelength 183 nm, then owing to the extremely high radiation density emitted into the water another quite special effect is experienced, namely that the oxygen dissolved in the irradiated water is converted directly, i.e. without passing through the gaseous phase, into ozone. This effect can be applied to great advantage to the combined treatment of the water by ozone action and UV action. In the course of this the fact (which is a disadvantage for ozone production in the gaseous phase) that the ozone formed under the influence of the wavelength 183 nm is broken down again by the simultaneously emitted wavelength of 254 nm, can now be turned to considerable advantage. For, the breakdown of the ozone takes place via the stage of atomic oxygen, so that in the water simultaneously with the intense sterilization effect of the wavelength of 254 nm, the very intense oxidizing effect of atomic oxygen is also available. Furthermore, through the breakdown of the ozone already taking place in the irradiation unit, the advantage is achieved that the output from the irradiation unit is once again free of ozone (and also of hydrogen peroxide, which can be formed by the reaction of ozone or atomic oxygen with water).

The presence of ozone or hydrogen peroxide in the water that has been treated is usually undesired, but is scarcely avoidable in a traditional ozonization by gaseous ozone. In unit 20 according to FIG. 7 and 8, however, it can be guaranteed in a simple manner that the water coming from the unit will not contain any traces of ozone or hydrogen peroxide which have not been made to vanish in the unit by wavelength 254 nm or by any oxidation processes that may be occurring. For this purpose the last lamp or lamps 1 in the direction of flow of the water (or the lamps in the last cascade chamber 31) along with their enveloping ducts 29 need only be made of a suitably doped quartz which does not transmit wavelengths around 183 nm, but only the wavelength region around 254 nm. Assuming that this last lamp or lamps 1 possess a sufficiently high radiation density of at least 150-200 mW/cm$^2$, they reliably break down all traces of ozone and hydrogen peroxide still remaining in the water just before its emergence from the unit.

The unit 20 represented in FIG. 7 and 8, taking into account the numerical example given above for lamps 1, has a width of about 80 cm and a height of about 18-20 cm. With this height, which corresponds to a distance of about 9-10 cm between one wide side of a lamp and a corresponding housing wall, the radiation will still have splendidly high intensity even in the vicinity of the housing wall, and even in the presence of highly contaminated water, an intensity which guarantees complete effectiveness of the radiation even in the vicinity of the housing wall. It should be noted here that the radiation intensity is decreased only by absorption along the path of the radiation and for geometric reasons hardly decreases at all with increasing distance from the lamps. In the extreme case the interior housing wall can be made highly reflective, but normally this is unnecessary.

The length of unit 20 in FIG. 7 and 8 depends on the number of lamps 1 present, which is governed in turn by the required water throughput. With three lamps 1 (in the case of the roughly 20×80 cm flow cross-section used in the numerical example) throughputs up to 100 m$^3$/h are possible, with 4 lamps up to 150 m$^3$/h and with 6 lamps up to 250 m$^3$/h. Here the individual lamps, as already mentioned, may be accommodated in the housing in a single irradiation chamber, or in several successive chambers 31 in cascade arrangement, in which case the orifice plates 26 may have e.g. 220 holes each of one cm diameter. With 6 lamps 1 this results in a maximum unit length of only about 40 cm. Such small unit dimensions with such high capacities are unattainable in principle with traditional lamps of round design.

A special advantage of this small structural size is that a comparatively large range of throughputs can be accepted by one and the same unit 20, by designing the unit for the upper limit of this range, (i.e. for a throughput of 250 m$^3$/h with 6 enveloping ducts for the acceptance of a maximum of six lamps 1) and then installing only as many lamps in the unit as are in fact needed for the specified throughput (e.g. only 3 or 4 lamps). In this way it is not necessary to construct a separate unit for every throughput capacity. Even very high throughputs, greater than 250 m$^3$/h, are possible with the flow cross-section of about 20×80 cm adopted above, provided the number of lamps is increased accordingly. However, since this necessitates sometimes undesirably high flow velocities of the water, it is generally more expedient for very high throughput capacities to connect two or more units 20 according to FIGS. 7 and 8 in parallel and place them e.g. one above the other. On account of the small structural size of the individual units, this presents no special problems.

Figure 10:
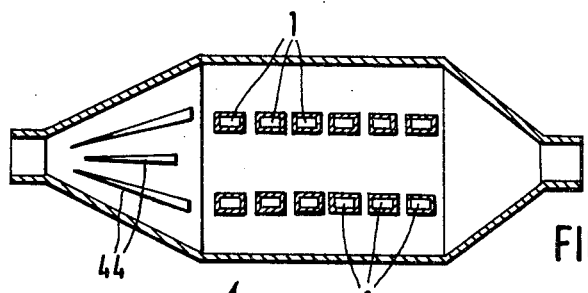
FIGS. 10 and 11 are schematic representations of two modified embodiments of the unit to FIGS. 7 and 8.
Figure 11:
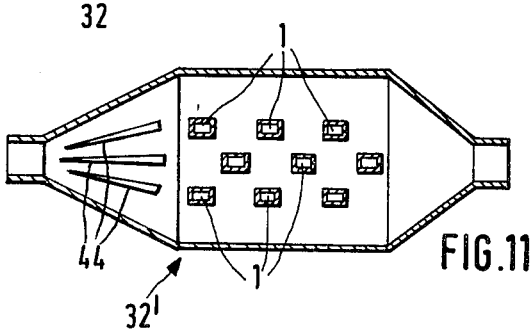

In FIG. 10 an alternative design of a unit 32 for very high throughput is represented in side elevation. This unit 32 is created by removing the intermediate housing walls between two units 20 according to FIG. 7 and 8 placed one above the other. Thus the successive lamps 1 are disposed in two vertically separated planes. Otherwise unit 32 corresponds to unit 20. Where necessary, unit 32 according to FIG. 10, of course, can have the lamps in three or more planes one above the other, and furthermore, the arrangements can be such (for reasons of fluid dynamics) that lamps 1 are staggered in relation to each other, as indicated in FIG. 11 for unit 32'.

In units 20, or 32 or 32' as the case may be, which are intended for moderate to high and very high throughput capacities, several lamps 1 in succession are disposed transversely to the direction of flow of the water. For small throughput capacities, generally a single, or not more than two lamps 1 suffice, and then it is expedient to align the lamps with the direction of flow of the water.

Figure 12:
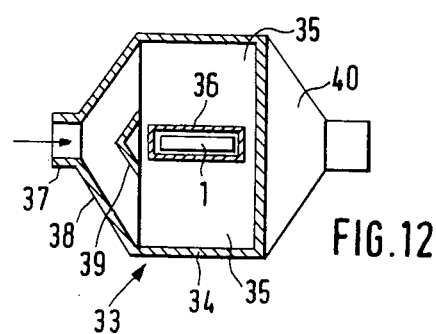
FIG. 12 is a schematic, sectional representation of another irradiation unit for flowing media.

An example of such a unit 33 with only a single lamp 1 is shown in FIG. 12. Unit housing 34 extends in the direction of flow of water, in the length of lamp 1, and enveloping duct 36 for the lamp is installed in the end wall of the housing in the manner described in FIG. 9. At one end of one wide side wall of the housing there is an inlet section 38 that is recognizable in FIG. 12. It distributes the water arriving from input pipe connection 37 to the two irradiation spaces 35 adjacent to the two wide sides of lamp 1. Enveloping duct 36 is covered inside inlet section 38 by a baffleplate 39. Outlet section 40 at the other end of unit housing 34 is similarly designed, but has no baffleplate 39.

Figure 13:
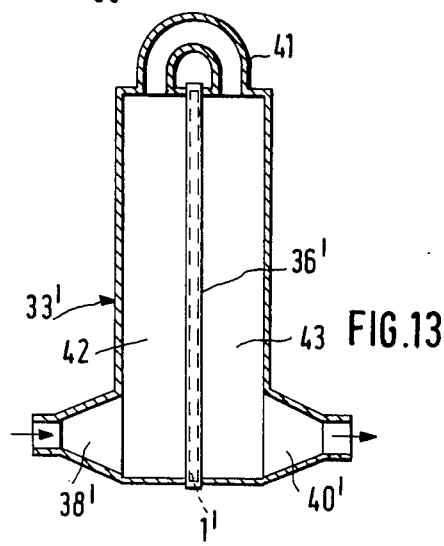
FIG. 13 is a schematic representation of a modified embodiment of the radiation unit according to FIG. 12.

A unit fitted with only one lamp can also be designed so that it possesses two irradiation chambers one after the other in cascade arrangement. This is illustrated in FIG. 13 for unit 33'. Unit 33' is for the most part similar to unit 33 according to FIG. 12, but in unit 33' enveloping duct 36' is sealed off along its two narrow sides from the respective wide side walls of the unit housing so that the interior space of the unit is divided into two separate irradiation channels 42 and 43. Here inlet section 38' and outlet section 40 are at the same end of the unit, located in the two narrow side walls, so that they are each in communication with only the one irradiation channel 42 or the other irradiation channel 43, while at the other end of the unit the two irradiation ducts are connected to each other through a connecting line 41. Thus the water flows through unit 33' successively first through an irradiation duct 42 and then through a second irradiation duct 43.

In unit 33' according to FIG. 13, a special bifunctional lamp 1' can also be used, one wide side of which, the one facing irradiation channel 42, consists of a quartz that also transmits wavelength 183 nm, while the other wide side, the one facing irradiation channel 43, is made from a suitably doped quartz which transmits only the wavelength 254 nm. By means of such a bifunctional lamp 1', the operational mode described above for unit 20 can also be carried out for unit 33'. In irradiation channel 42 the generation of ozone with simultaneous ozone breakdown takes place in the irradiated water, and in the subsequent irradiation channel 43 the reliable breakdown of all remaining traces of ozone then takes place. In this case enveloping duct 36', of course, must be adapted as far as its UV-permeability is concerned to the spectrum emitted by lamp 1', and in addition to this, the condition that lamp 1' delivers a sufficiently high radiation density of at least 150–200 mW/cm$^2$ on both sides must be satisfied. The manufacture of such bifunctional lamps 1', the two wide sides of which are made from materials of different transmissivity, has become possible for the first time owing to the invention, since the combining (fusion) of the materials of different transmissivity can be carried out in the region of the narrow sides of lamp 1, which are in any event of no importance as far as the emitted radiation is concerned.

Figure 14:
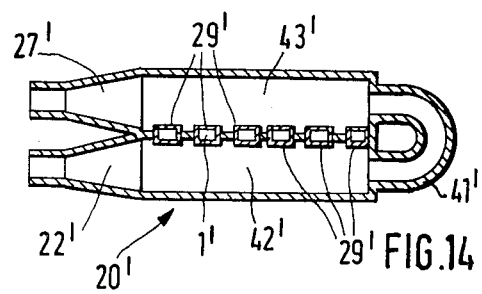
FIG. 14 is a schematic representation of another modified embodiment of the unit according to FIGS. 7 and 8.

Bifunctional lamps 1' of the type described above, which emit the wavelengths 183 nm and 254 nm on one wide side, and only the wavelength 254 nm on the other wide side, can be used together with correspondingly designed enveloping ducts in a multi-lamp unit 20' of the type described in FIG. 7 and 8 for unit 20, if it is ensured, as in the case of unit 33', that the water flows in a definite manner first through an irradiation channel 42' on one side of the lamp and then through a second irradiation channel 43' on the other side of the lamp, and if the radiation of 183 nm and 254 nm is assigned to the irradiation channel through which it flows first, and the radiation of 254 nm only is assigned to the irradiation channel through which it flows subsequently. This is represented schematically in FIG. 14. It can be seen there that the enveloping ducts 29' of lamps 1' are disposed basically in the manner shown in FIGS. 7 and 8, but are reciprocally sealed on their narrow sides, so that the two separated irradiation channels 42' and 43' are formed in the unit. These two irradiation channels are connected to each other via a connecting line 41' at one end of the unit, and are connected at the other end of the unit separately to inlet section 22' and outlet 27' respectively. In its operation, unit 20' corresponds to unit 33'.

The invented units have been described above in reference to the UV-irradiation of water for purposes of sterilization, but it is obvious that they can also be used for the irradiation of other liquid or gaseous media with a view to producing photo-reactions therein. To this extent all the numerical dimensions given above for the units and the lamps, the throughputs of the units and the number of lamps per unit are not obligatory for the invention, but serve only to illustrate a concrete embodiment thereof. These numerical values, for another application of the unit, can depart from the values given above to a greater or lesser extent. Moreover, the design of the units can be modified in many respects without going outside the scope of the invention. Thus, for example, The inlet sections of the units, as indicated in FIGS. 10 and 11, may be designed as an ordinary inlet cone with flow guide plates 44 installed in it for the distribution of the incoming medium, or additional flow-guiding elements can be incorporated in the units in order to produce as laminar a flow as possible, or perhaps as turbulent a flow as possible. Nor do the units have to have a strictly rectangular cross-section, but can have e.g. slightly rounded-off edges. Finally, lamps 1 do not absolutely have to emit the wavelengths 183 nm or 254 nm as the case may be, but lamps with different ranges or radiation can be used where this is required for the given intended photo-reaction. However, it is important here for the lamp tube to be designed with a flat, elongated cross-section and elongated electrodes so as to be able to emit a higher radiation density.

What is claimed is:

1. Irradiation apparatus including a low-pressure mercury lamp suitable for photochemical disinfecting and sterlization, said lamp including a lamp tube having a flat, elongated cross-section and including electrodes extending along the width direction of said lamp tube, wherein the improvement in said irradiation apparatus comprises:

an outer enveloping tube substantially surrounding said lamp tube in spaced relation thereto and having a shape substantially conforming to the shape of said lamp tube; and duct means passing through said enveloping tube and formed and positioned along the narrow sides of said lamp tube for the discharge and withdrawal of a fluid medium into the space between said lamp tube and said enveloping tube along said narrow sides.

2. The irradiation apparatus as defined in claim 1 wherein, the two wide sides of said lamp tube are made from materials having different radiation transmissivities; and said enveloping tube and duct means are formed for progressive exposure of said medium first to one wide side of said lamp tube and then to the remaining wide side of said lamp tube.

3. The irradiation apparatus as defined in claim 1 wherein, said duct means are provided by two conduits with one of said conduits positioned between each of the narrow sides of said lamp tube and said enveloping tube.

4. The irradiation apparatus as defined in claim 3 wherein, said two conduits extend substantially over the length of said lamp tube.

5. The irradiation apparatus as defined in claim 3 wherein, said two conduits terminate in open ends proximate one end of said lamp tube; and said duct means further includes a third conduit extending into and communicating with the space between said lamp tube and said enveloping tube proximate an opposite end of said lamp tube.

6. The irradiation apparatus as defined in claim 4 wherein, said two conduits are formed with nozzle means formed to direct the flow of said fluid medium parallel to the wide side of said lamp tube.

7. The irradiation apparatus as defined in claim 6 wherein, said nozzle means are formed to direct the flow of said fluid medium transversely to the length of said lamp tube.

8. The irradiation apparatus as defined in claim 4, and half-shell means mounted proximate each of said two conduits and formed to define an annular gap around the narrow sides of said lamp tube, said conduits being formed for the communication of said fluid medium to said gap for flow around said lamp tube.

9. The irradiation apparatus as defined in claim 1 wherein, said enveloping tube is sealed to said lamp tube to permit immersion of said apparatus in a material to be treated, and said duct means includes a discharge outlet positioned for discharge of irradiated fluid medium into said material when said apparatus is immersed in said material.

* * * * *